US009957396B2

(12) United States Patent
Huen et al.

(10) Patent No.: US 9,957,396 B2
(45) Date of Patent: May 1, 2018

(54) DURABLE ANTIMICROBIAL COATING COMPOSITION

(71) Applicant: Nano and Advanced Materials Institute Limited, Hong Kong (HK)

(72) Inventors: Ngar Yee Huen, Hong Kong (HK); Connie Sau Kuen Kwok, Hong Kong (HK); Wah Kit Cheuk, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 477 days.

(21) Appl. No.: 14/555,596

(22) Filed: Nov. 27, 2014

(65) Prior Publication Data

US 2016/0032113 A1 Feb. 4, 2016

Related U.S. Application Data

(60) Provisional application No. 61/999,576, filed on Jul. 31, 2014.

(51) Int. Cl.
| | |
|---|---|
| *C09D 5/14* | (2006.01) |
| *C03C 17/10* | (2006.01) |
| *C03C 17/32* | (2006.01) |
| *C04B 41/88* | (2006.01) |
| *B05D 7/00* | (2006.01) |
| *C04B 41/00* | (2006.01) |
| *C04B 41/51* | (2006.01) |
| *A01N 47/44* | (2006.01) |
| *A01N 59/16* | (2006.01) |
| *A61L 2/00* | (2006.01) |
| *A61L 9/00* | (2006.01) |
| *B05B 7/00* | (2006.01) |
| *C04B 111/20* | (2006.01) |

(52) U.S. Cl.
CPC .............. *C09D 5/14* (2013.01); *A01N 47/44* (2013.01); *A01N 59/16* (2013.01); *A61L 2/00* (2013.01); *A61L 9/00* (2013.01); *B05B 7/00* (2013.01); *C03C 17/10* (2013.01); *C03C 17/32* (2013.01); *C04B 41/009* (2013.01); *C04B 41/5116* (2013.01); *C04B 41/88* (2013.01); *C04B 2111/2092* (2013.01)

(58) Field of Classification Search
CPC ........... C09D 5/14; C03C 17/10; C03C 17/32; C04B 41/5116; C04B 41/4535; C04B 41/4549; C04B 41/5188; C04B 41/88; B05D 7/00; A01N 59/16; A01N 47/44; A01N 25/10
See application file for complete search history.

(56) References Cited

U.S. PATENT DOCUMENTS

| | | | | |
|---|---|---|---|---|
| 6,464,764 B1 * | 10/2002 | Lichtenberg | ........... | A01N 55/00 106/15.05 |
| 2009/0011160 A1 * | 1/2009 | Paulussen | .............. | B05D 3/144 428/34.8 |
| 2010/0062032 A1 | 3/2010 | Sharma | | |
| 2011/0111213 A1 | 5/2011 | Es-Souni | | |

FOREIGN PATENT DOCUMENTS

| CN | 102726395 A | * 10/2012 |
|---|---|---|
| EP | 1681325 | 12/2006 |

OTHER PUBLICATIONS

First Office Action with search report issued by the State Intellectual Property Office of China dated Feb. 14, 2017.
Natarajan Velmurugan et al., "Synthesis and Characterization of Potential Fungicidal Silver Nano-sized Particles and Chitosan Membrane Containing Silver Particles", Iranian Polymer Journal, vol. 18, No. 5 (2009), p. 383-392.
Dongjo Kim and Jooho Moon, Highly Conductive Ink Jet Printed Films of Nanosilver Particles for Printable Electronics, Electrochemical and Solid-State Letters 8 (2005) J30-J33.
Leceta, et al., Characterization and antimicrobial analysis of chitosan-based films, Journal of Food Engineering 116. (2013) 889-899.
Pauline Cordenonsi Bonez, et al., Chlorhexidine activity against bacterial biofilms, American Journal of Infection ControL 41 (2013) e119-e122.
Christopher G. Jones, Chlorhexidine: Is it still the gold standard, Periodontology 2000 15 (1997) 55-62.
Second Office Action issued from the State Intellectual Property Office of the People's Republic of China dated Jul. 19, 2017.
Zihong Zhang et al., Study on germicidal efficacy and toxicity of compound disinfectant gel of nanometer silver and chlorhexidine acelate, Chinese Journal of Health Laboratory Technology, Aug. 31, 2007, pp. 1403-1404 & 1430, vol. 17, No. 8, China Academic Journal Electronic Publishing House, the PRC.

* cited by examiner

*Primary Examiner* — John Pak
*Assistant Examiner* — Nathan W Schlientz
(74) *Attorney, Agent, or Firm* — Spruson & Ferguson (Hong Kong) Limited

(57) ABSTRACT

The presently claimed invention provides a coating composition for an antimicrobial coating, and a method for synthesizing the coating composition. A coating method for deposition of the antibacterial coating is also provided. The antimicrobial coating of the present invention is effective in providing antimicrobial function, easy to be manufactured, stable and durable.

9 Claims, 13 Drawing Sheets

DURABLE ANTIMICROBIAL COATING COMPOSITION

CROSS REFERENCE TO RELATED APPLICATION

Pursuant to 35 U.S.C. § 119(e), this is a non-provisional patent application which claims benefit from U.S. provisional patent application Ser. No. 61/999,576 filed Jul. 31, 2014, and the disclosure of which is incorporated herein by reference.

FIELD OF THE INVENTION

The present invention relates to a coating, and particularly relates to a durable antimicrobial coating. The present invention also relates to a coating composition and preparation method for forming said coating.

BACKGROUND

An antimicrobial coating contains an antimicrobial agent that kills, inhibits or reduces the ability of bacteria to grow on the surface of the coating. Antimicrobial coating composition is usually in a form of a liquid formulation which is applied on surfaces and dried to form a coating. Such coating is getting widely used in various areas including clinics, industry, and even home. One of the most commonly used areas with antimicrobial coatings is in clinic or hospital since the antimicrobial coatings are able to reduce the risk of disease transmission.

It is well known in the art that titanium dioxide and silver are commonly used to form antibacterial coatings. US2010/0062032 discloses a doped titanium dioxide coating composition for antimicrobial coatings, and the preferred dopants are silver and silver oxide.

US2011/0111213 also discloses a silver (Ag)-ion containing titanium (Ti) oxide coating composition having a silver content of greater than or equal to 0.2 of Ag/l of Ti to less than or equal to 0.4 of Ag/l of Ti, wherein the coating composition is X-ray amorphous and the hydrophobicity of the coating composition can be reduced persistently by illumination. A process for producing the coating comprises the steps of preparing a $TiO_2$—Ag solution, coating a carrier material using the $TiO_2$—Ag solution, and curing the $TiO_2$—Ag solution that has been applied to the carrier, using a temperature equal or less than 200° C.

EP1681325 discloses a coating material which comprises titanium dioxide as a photocatalyst, apatite comprising calcium phosphate for adsorbing contaminants, a polymethoxy polysiloxane as a hydrophilic resin coating material, and also a thiosulfato silver complex as an antibacterial material. The coating formed by the coating material can convert pollutants such as various bacteria to harmless materials.

Nevertheless, the coatings from the abovementioned prior arts involve complicated process in synthesis of the coating solution. The synthesis of these conventional coatings requires elevated temperature to cure the coating solution, which increases the cost and may deteriorate the properties of the coating. In addition, some of the prior arts fail to provide coatings with high transparency, which limits the application of coating. Furthermore, these conventional coatings are easily peeled off after a period of usage, ultimately losing their functions.

Consequently, there is a need for an antimicrobial coating composition which is effective in providing antimicrobial function, easy to be manufactured, durable, stable and can be cured or dried on surface without high temperature curing.

SUMMARY OF THE INVENTION

Accordingly, a first aspect of the presently claimed invention is to provide a coating composition for an antimicrobial coating.

In accordance with an embodiment of the first aspect of the presently claimed invention, the coating composition comprises chitosan, chlorhexidine, silver nanoparticles, chitosan cross-linker and water.

A second aspect of the presently claimed invention is to provide a method for synthesizing a coating composition for an antimicrobial coating.

In accordance with an embodiment of the second aspect of the presently claimed invention, the method for synthesizing a coating composition for coating a surface for antimicrobial effect comprises providing silver nanoparticle dispersion and chlorhexidine, dissolving chitosan in an acidic organic solvent to form a chitosan solution, incubating a chitosan cross-linker with the chitosan solution to form a solution of crosslinked chitosan, mixing the silver nanoparticle dispersion and chlorhexidine with the solution of crosslinked chitosan to form said coating composition suitable for coating on a surface for antimicrobial application. In one embodiment, the resulting coating composition according to this embodiment may comprise in percentage by weight to volume (w/v) of 0.001% silver nanoparticles, 0.800% chitosan, 0.800% acetic acid for dissolving the chitosan, 0.200% chlorhexidine, 0.24% glutaraldehyde as the chitosan crosslinker and 97.96% water.

Unlike the traditional antimicrobial coating composition, the antimicrobial coating composition of the presently claimed invention provides several advantages. Surfaces coated with the antimicrobial coating composition of the present invention is effective in removal of wide range of microorganisms, and can be applied on a wide range of surfaces as it can be cured or dried at room temperature without curing at high temperatures which is often required by conventional coating compositions. Additionally, the antimicrobial coating composition of the present invention increases durability to the surface coated therewith and the coating composition possesses strong adhesion property to the surface being coated. The antimicrobial coating composition of the present invention is high in transparency and only thin layer is required for sufficient antimicrobial function.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

Figure 1A:
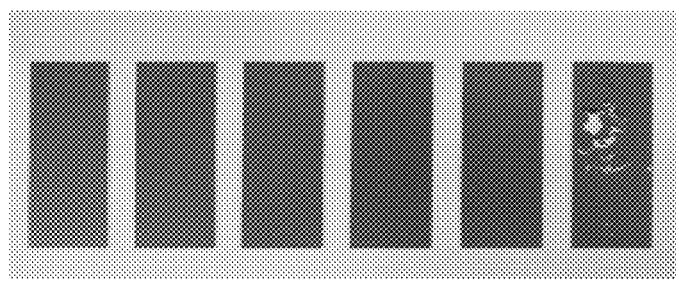
FIG. 1 are glass (FIG. 1A), plastic (FIG. 1B), metal (FIG. 1C), painted wood (FIG. 1D) and ceramic (FIG. 1E) surfaces coated with a coating composition of the present invention having wiped with water for 0-20 times.

In the following description, a coating composition for an antimicrobial coating, a method for synthesizing the coating composition, and a method for deposition of the antimicrobial coating are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

According to an embodiment of the presently claimed invention, a coat composition for forming a durable, antimicrobial coating on a surface comprises chitosan, chlorhexidine, silver nanoparticles, chitosan cross-linker and water is provided. In one embodiment, the coating composition comprises (w/v) 0.0002%-0.001% of silver nanoparticles, 0.48%-1.9% chitosan, 0.48-1.9% acetic acid, 0.05%-0.2% chlorhexidine, 0.06%-0.35% glutaraldehyde and water. The percentage of water will be added to adjust the total volume to 100%. In one embodiment, the coating composition comprises 0.001% silver nanoparticles, 0.80% chitosan, 0.80% acetic acid, 0.20% chlorhexidine, 0.24% glutaraldehyde and 97.96% water. In one embodiment, the chitosan is a low molecular weight crosslinked chitosan.

The present coating composition does not require curing at high temperatures. The present coating composition can be dried on the surface coated therewith forming an antimicrobial coating at room temperature in less than 60 mins. In one embodiment, the coating composition is dried on the surface coated therewith and forming an antimicrobial coating within 30 mins, or within 5 mins.

The present coating composition forms a highly antimicrobial coating that is effective to kill >99.9% of most microbes within 5 mins and also inhibit growth of the microbes. It is demonstrated that a surface coated with the present coating composition can eliminate about 99.9% of H1N1 influenza A virus in 10 mins. The surface coated with the present coating composition kills at least 99.99% of *E. coli* in 5 mins. The surface coated with the present coating composition can inhibit growth of moulds and fungi for at least 6 weeks. Antimicrobial capability of the present coating composition is further illustrated in the working examples below.

The present coating composition results in a highly durable coating on a wide range of surfaces. The antimicrobial coating formed from the present coating composition remains on the surface coated therewith for at least 3 months without any mechanical or chemical removal. The coating formed from the present coating composition is resistant to cleaning agents, such as water, alcohol and bleach. The coating remains on the surface after wiping with water, alcohol or bleach for at least 15 times. The coating formed from the present coating composition resists wiping with 70% ethanol and 1:49 bleach solution. A thin layer of the present coating composition is sufficient for antimicrobial effects. In one embodiment, 8.5 µl/cm$^2$ of the present coating composition is sufficient to give effective antimicrobial effect. The present coating composition and the coating formed therefrom are transparent. If desired, coloured pigment, dyes, coloured paint may be included in the present coating composition such that the coating becomes coloured. The present coating composition complies with the restriction of hazardous substances directive (RoHS) and substances of very high concern (SVHC) tests. The RoHS test examines the mercury, cadmium, lead, hexavalent chromium, PBBs, PBDEs content for the limits as specified in 2011/65/EU Directive. The SVHC test examines 151 candidate substances listed in Regulation No. 1907/2006 in European Chemicals Agency.

The present coating composition is suitable for applying on a wide range of surfaces. The surfaces on which the present coating composition may be applied include, but are not limited to, plastic, glass, metal, non-metal, wood and painted surfaces. The present coating composition may be applied by any conventional coating or deposition methods. For example, the present coating composition may be applied on surfaces by spraying, spreading and wiping.

According to a second embodiment of the presently claimed invention, a method for synthesizing a coating composition for coating a surface for antimicrobial effect is provided. The present method comprises steps of providing silver nanoparticle dispersion and chlorhexidine, dissolving chitosan in an acidic organic solvent to form a chitosan solution, incubating a chitosan cross-linker with the chitosan solution to form a solution of crosslinked chitosan, mixing the silver nanoparticle dispersion and chlorhexidine with the solution of crosslinked chitosan to form said coating composition suitable for coating on a surface for antimicrobial application. The acidic organic solvent suitable for dissolving chitosan includes, but is not limited to, acetic acid and ethanol.

Chlorhexidine is not water soluble. The chlorhexidine in the present method for synthesizing a coating composition is dissolved in an organic solvent. The chlorhexidine may be dissolved in ethanol. Other organic solvents available in the art may be used to dissolve chlorhexidine in synthesizing the coating composition of the present invention.

In one embodiment, the coating composition comprises (w/v) 0.0002%-0.001% of silver nanoparticles, 0.48%-1.9% chitosan, 0.48-1.9% acetic acid, 0.05%-0.2% chlorhexidine, 0.06%-0.35% glutaraldehyde and water. The percentage of water will be added to adjust the total volume to 100%. In one embodiment, the coating composition according to this embodiment may comprise 0.001% silver nanoparticles, 0.800% chitosan, 0.800% acetic acid for dissolving the chitosan, 0.20% chlorhexidine, 0.24% glutaraldehyde as the chitosan crosslinker and 97.96% water.

In accordance with another embodiment of the presently claimed invention, the method for deposition of an antimicrobial coating comprises steps of preparing the coating composition of the presently claimed invention, providing an object; applying the coating composition onto at least a surface of the object to form one or more coating layers; and drying the one or more coating layers at room temperature. The present coating composition can be dried at room temperature in 5 minutes. In one embodiment, the coating composition is deposited at a concentration of 8.5 μl/cm$^2$ onto a surface to form an antimicrobial coating. The applying step comprises spraying, spreading, wiping or combination thereof that are readily done in the art. Spraying may be done by a spray gun. The coating composition is sprayed onto the substrate in one direction to form a first layer. The coating composition is then sprayed onto the substrate in a direction 90° to the original direction to form a second layer and the coating composition is further sprayed onto the substrate in a direction 90° to the direction of the second layer to form a third layer until a desired concentration of coating composition is coated onto the substrate. Spreading means the coating composition is added onto the substrate is evenly spread onto the substrate and leave to dry. Wiping is when the coating composition is added onto the substrate and the coating composition is wiped over the substrate until the composition is dried.

EXAMPLES

Preparation of the one exemplary embodiment of the present coating composition is illustrated below.

Preparation of Silver Nanoparticles (AgNPs) and 0.1% AgNPs Dispersion

Polyvinylpyrrolidone (36.42 g) is dissolved in ethylene glycol (75 ml) under 120° C. for 30 mins by stirring to obtain Solution A. Silver nitrate (5.8 g) is dissolved in ethylene glycol (25 ml) at room temperature for 30 min by stirring to obtain Solution B. Solution A and Solution B are mixed at room temperature to obtain AgNPs solution. The AgNPs solution is washed with 1 L acetone and 100 ml ethanol for 4 times by centrifugation at 18,671 g. The precipitate is then dried under room temperature to obtain the silver nanoparticles.

The AgNPs (1 mg) is dispersed into deionized water (1 ml) to obtain 0.1% AgNPs dispersion.

Preparation of 1% (w/v) Chitosan Solution

Low molecular weight chitosan (1 g) is dissolved into acetic acid (1 ml) and deionized water (99 ml) with stirring overnight to obtain a chitosan solution.

Preparation of 10 mg/ml Chlorhexidine Dispersion in Water

Chlorhexidine (10 mg) is weighed and 100 μl absolute ethanol is added to dissolve chlorhexidine. Deionized water (900 μl) is then added to adjust chlorhexidine concentration to 10 mg/ml.

Preparation of 12% Glutaraldehyde Solution

25% glutaraldehyde (1 ml) is diluted with deionized water (1.08 ml) to prepare 12% glutaraldehyde solution.

Preparation of Antibacterial Coating (ABC)

12% glutaraldehyde solution (100 μl) is mixed with 1% chitosan solution (4 ml), and the mixture is incubated at room temperature for at least 30 min to cross-link the chitosan. The 0.1% AgNPs dispersion (50 μl) is then added into the cross-linked chitosan. 10 mg/ml chlorhexidine dispersion in water (1 ml) is further added to the AgNP/cross-linked chitosan to obtain the coating composition of the present invention. 2 mg/ml chlorhexidine is present in the coating composition. Table 1 shows the content of the coating composition of the present invention in percentage by volume.

| Ingredients | AgNPs (w/v) | Chitosan (w/v) | Acetic acid (v/v) | Chlorhexidine (v/v) | Glutaraldehyde (v/v) | Water (v/v) |
| --- | --- | --- | --- | --- | --- | --- |
| Percentage | 0.001% | 0.80% | 0.80% | 0.20% | 0.24% | 97.96% |

Table 1 shows content of one embodiment of the present coating composition

A coating composition of Table 1 are coated on different substrates (glass, plastic, metal, painted wood and ceramics). Resistance and antibacterial properties are tested.

Example 1—Resistance on Various Substrate

Figure 1B:
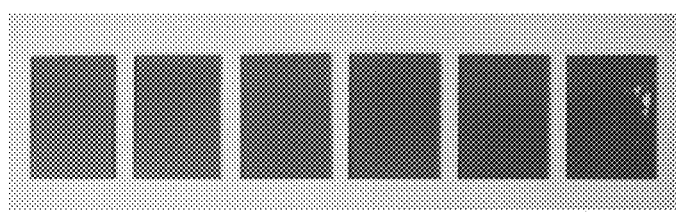
Figure 1C:
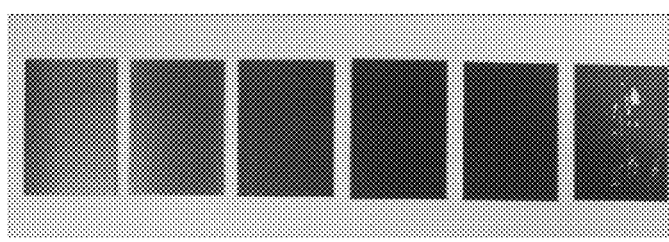
Figure 1D:
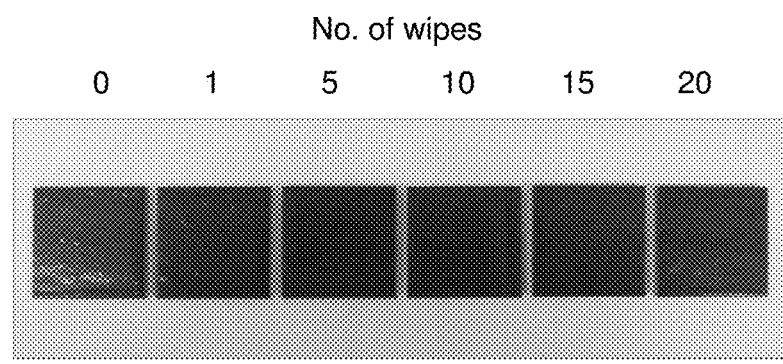
Figure 1E:
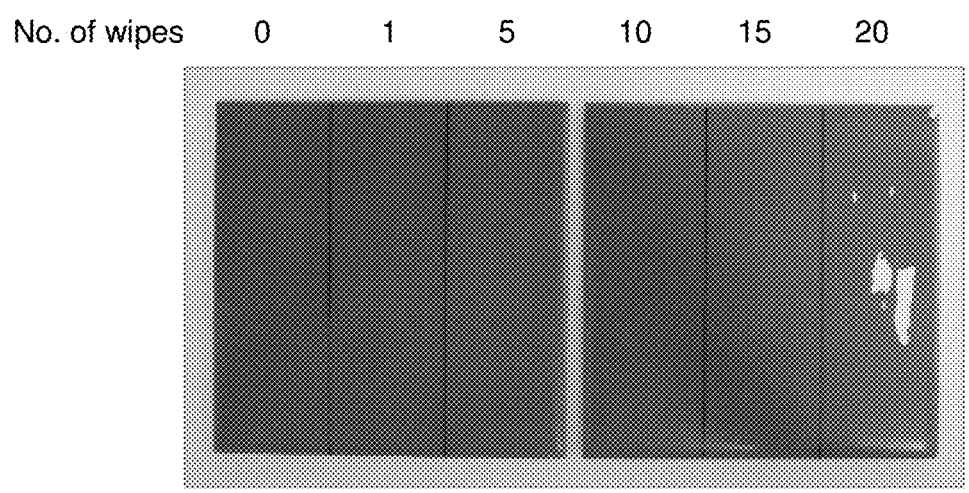
Figure 2A:
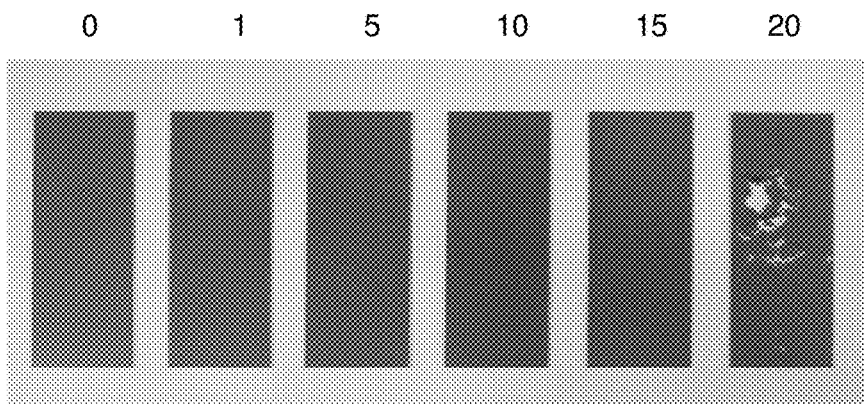
FIG. 2 are glass surface coated with a coating composition of the present invention having wiped with water (FIG. 2A), 70% IPA (FIG. 2B) and 1:49 water diluted bleach solution (FIG. 2C) for 0-20 times.
Figure 2B:
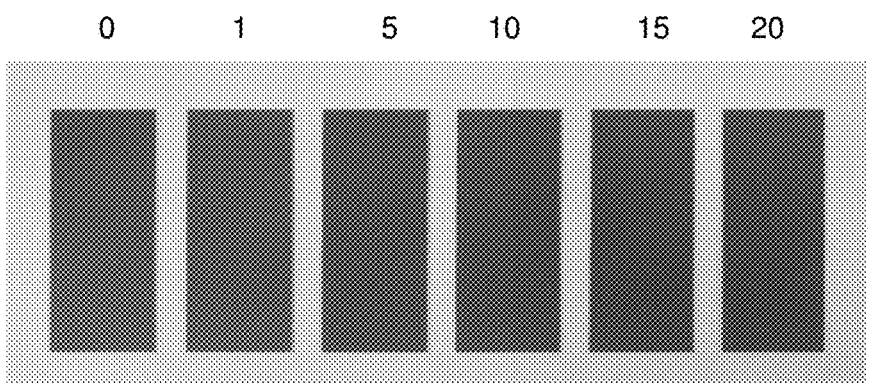
Figure 2C:
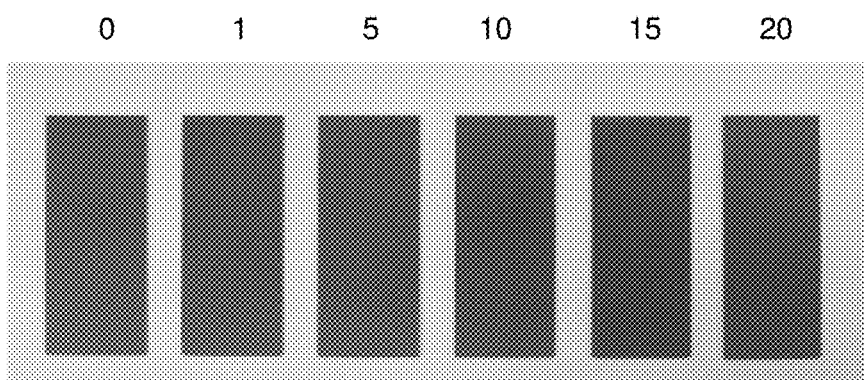
Figure 3:
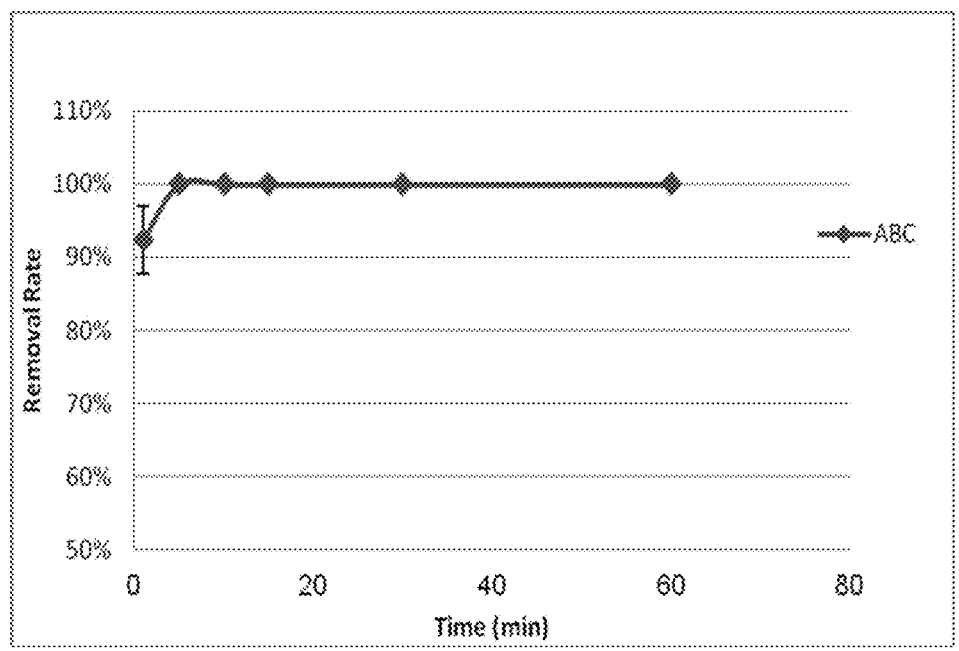
FIG. 3 is a graph showing the bacterial removal rate of surfaces coated with a coating composition of the present invention (ABC—antimicrobial coating of the present invention)
Figure 4:
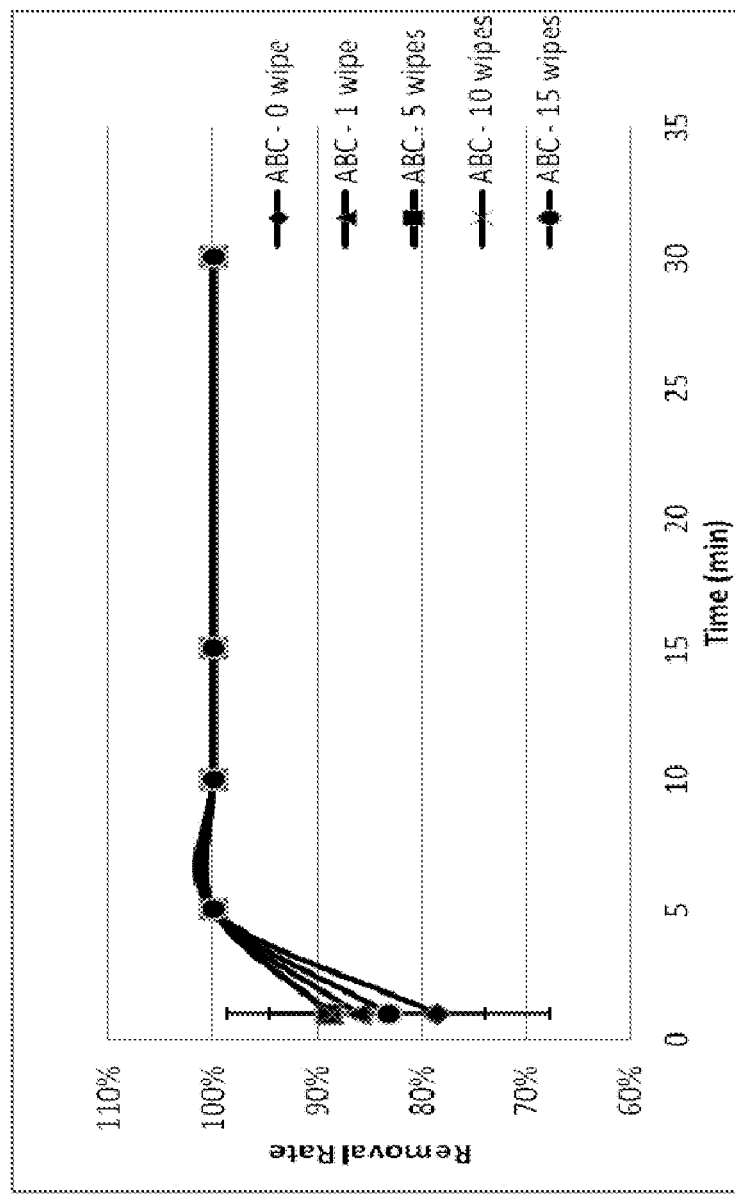
FIG. 4 is a graph showing the bacteria removal rate of glass surfaces coated with a coating composition of the present invention and having wiped with water for 0-15 times.

The coating composition of the present invention is transparent when dried. Blue dye is added for easy visualization. 48 μl/cm$^2$ of the present coating composition is sprayed on five substrates. Upon coating formation, the coating is wiped with water once every day for 20 consecutive days. The number of wipes and the appearance of the coating are observed in FIG. 1. 1-25% of coating is removed after 20 wipes with water on glass (FIG. 1A), plastic (FIG. 1B), metal (FIG. 1C) and ceramics (FIG. 1E). The present coating remains intact on wood painted with lacquer after wiping with water for 20 times (FIG. 1D). Results show that coating formed from the present coating composition can withstand mechanical wiping with water for at least two weeks.

Example 2—Resistance to Water, Alcohol and Bleach

Common cleaning agents, such as water, 70% isopropyl alcohol (IPA) and 1:49 diluted bleach solution, are used readily for wiping surfaces. Capabilities of the present coating composition to resist against these common cleaning agents are tested. 48 μl/cm$^2$ of the present coating composition is sprayed on glass substrate and is wiped with three cleaning agents once every day for 20 consecutive days. As seen in FIGS. 2A-2C, 1-25% of the coating is removed after 20 times of wiping with water, whereas the coating remains intact after 20 times of wiping with 70% IPA and bleach solution. The results show that coating formed from the present coating composition can withstand common cleaning agents.

Example 3—Antimicrobial Efficiency—*Escherichia coli*

*E. coli* is used as a representative of gram-negative bacterium. The coating composition's antimicrobial effect against *E. coli* is tested. *E. coli* suspension at 5×10$^4$ cells/2 ml is spread onto surface of a glass petri dish (area 23.7 cm²) deposited with 8.5 μl/cm² of the present coating composition, and onto an uncoated petri dish as a control sample. Samples are then incubated at room temperature for 1 hour. The bacteria removal rates at specified time points are then determined. The bacterial removal rate is the bacterial count of the coated petri dish to the bacterial count of the uncoated petri dish. The experiment is done for 3 times. Results are shown in Table 2 below and FIG. 3.

| Elapsing time | Bacteria removal rate | | | |
|---|---|---|---|---|
| | Set 1 | Set 2 | Set 3 | Average |
| 1 min | 95.60% | 87.00% | 94.44% | 92.35% |
| 5 min | 100.00% | 100.00% | 100.00% | 100.00% |
| 10 min | 100.00% | 100.00% | 100.00% | 100.00% |
| 15 min | 100.00% | 100.00% | 100.00% | 100.00% |
| 30 min | 100.00% | 100.00% | 100.00% | 100.00% |
| 1 hour | 100.00% | 100.00% | 100.00% | 100.00% |

Table 2 shows the antibacterial activity against *E. coli* of surfaces coated with the present coating composition The coating formed from the coating composition of the present invention is shown to kill *E. coli* in 5 mins. It is demonstrated that the present coating composition is effective in killing at least 99.99% of bacteria within 5 mins. The antimicrobial property of the present coating composition after surface cleaning is further examined. Glass petri dishes deposited with 8.5 μl/cm² of the present coating composition are wiped with water for 0, 1, 5, 10, 15 times. Samples are then subject to antimicrobial test against *E. coli*, an uncoated petri dish is tested together as a control. Results are shown in Table 3 below and FIG. 4.

| Elapsing time | Bacteria removal rate | | | | |
|---|---|---|---|---|---|
| | 0 wipe | 1 wipe | 5 wipes | 10 wipes | 15 wipes |
| 1 min | 80.00% | 87.90% | 87.10% | 89.12% | 88.07% |
| 5 min | 100.00% | 100.00% | 100.00% | 100.00% | 100.00% |
| 10 min | 100.00% | 100.00% | 100.00% | 100.00% | 100.00% |
| 15 min | 100.00% | 100.00% | 100.00% | 100.00% | 100.00% |
| 30 min | 100.00% | 100.00% | 100.00% | 100.00% | 100.00% |
| 1 hour | 100.00% | 100.00% | 100.00% | 100.00% | 100.00% |
| 2 hours | 100.00% | 100.00% | 100.00% | 100.00% | 100.00% |

Table 3 shows the antibacterial activity against *E. coli* of surfaces coated with the present coating composition after wiping with water Coating formed from the present coating composition is also capable to eliminate 100% *E. coli* within 5 mins after wiping with water. It is shown that the coating is resistant to water and water has no effect on the antimicrobial activity of the coating.

Example 4—Antibacterial Activity of the Coating by Different Coating Method

The antibacterial efficiency of the coating formed by depositing the present coating composition by different method is investigated. (1) one set of glass petri dish (surface area: 23.7 cm²) is sprayed with 2, 6 and 10 layers of the present coating composition at 3.2 μl/cm² per layer. Another set of petri dish is spread with 8.5 μl/cm² of the present coating composition. Each set of petri dishes are performed in triplicates. Average bacterial removal rates of the two sets of petri dishes are shown in Table 4 below and FIG. 5A.

| Elapsing time | Average bacteria removal rate | | | |
|---|---|---|---|---|
| | Spreading | Spraying | | |
| | | 2 layers | 6 layers | 10 layers |
| 1 min | 92.35% | 34.01% | 60.87% | 74.62% |
| 5 min | 100.00% | 70.21% | 93.42% | 99.75% |
| 10 min | 100.00% | 77.65% | 98.50% | 100.00% |
| 15 min | 100.00% | 86.05% | 99.90% | 100.00% |
| 30 min | 100.00% | 98.42% | 100.00% | 100.00% |
| 1 hour | 100.00% | 100.00% | 100.00% | 100.00% |

Table 4 shows the antibacterial activity against *E. coli* of surfaces coated with the present coating composition using different application means The results show that glass surface coated with 2 layers of the present coating composition remove 100% bacteria in 1 hour; 6 layers remove 100% of bacteria in 30 minutes and 10 layers remove all bacteria in 10 minutes. The antimicrobial activity of the coating composition is directly proportional to the amount applied. Coating the coating composition by spreading is shown to have a greater antibacterial activity as spreading method can fully cover the glass petri dish with the coating composition.

Figure 5A:
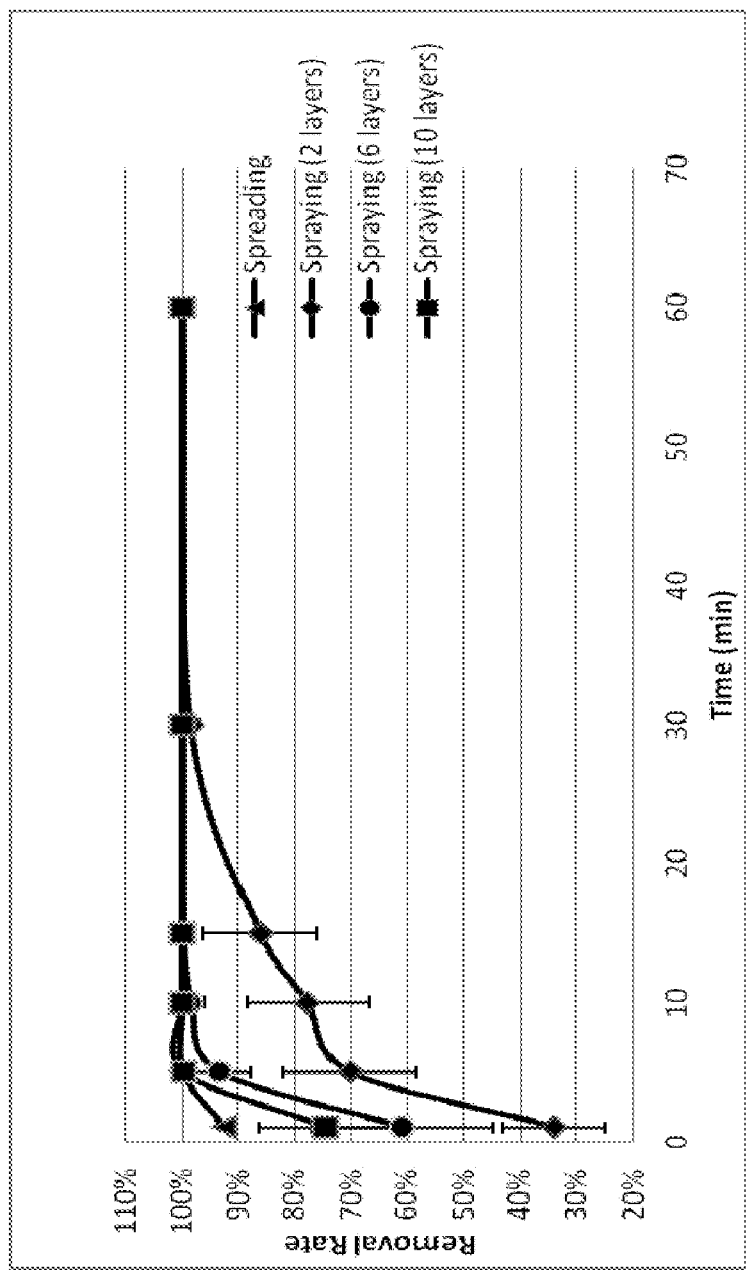
FIG. 5 are graphs showing the bacterial removal rate of glass surfaces coated with a coating composition of the present invention by different deposition means: spreading or spraying in different number of layers of the coating composition (FIG. 5A); and spreading, wiping to disperse or wiping to dry (FIG. 5B)
Figure 5B:
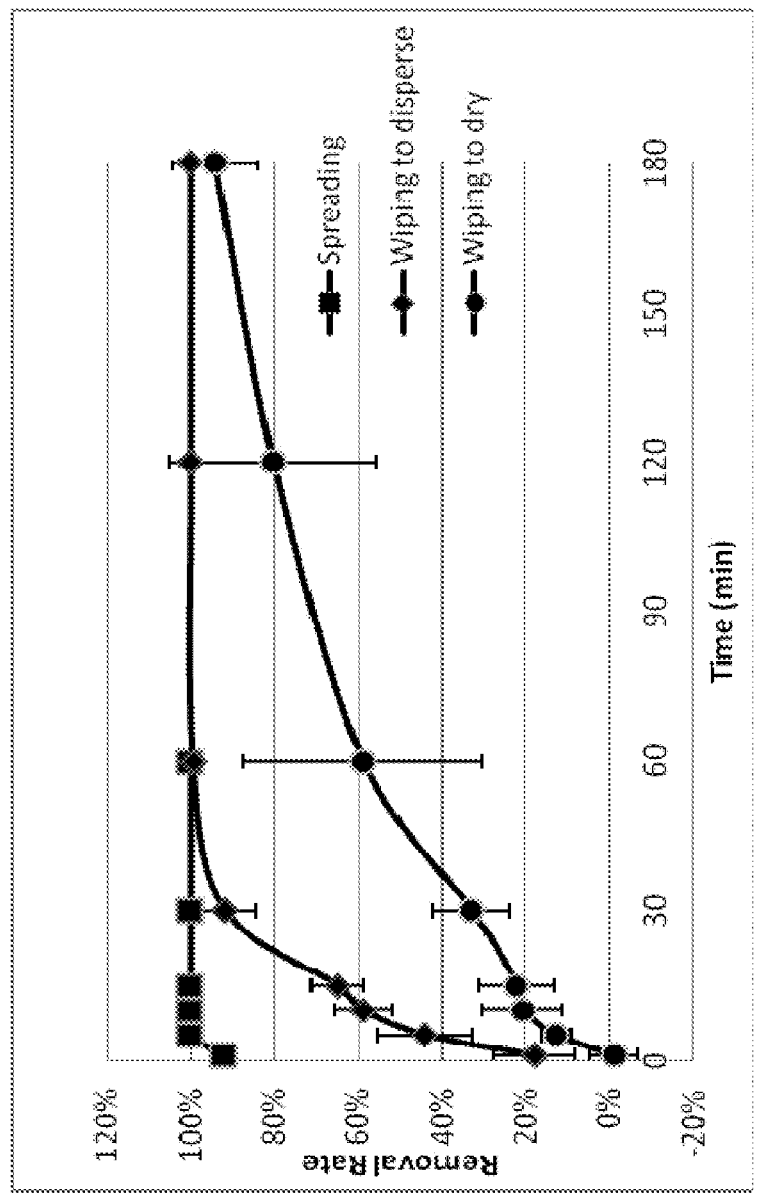

(2) The present coating composition is applied onto glass petri dish (surface area; 23.7 cm²) by dripping 202 μl (to give 8.5 μl/cm²) of the coating composition and wiping the glass surface with tissue paper to disperse the coating composition evenly and allow to be air dried at room temperature. Same amount of coating composition is dripped onto glass petri dish and the surface is wiped with tissue paper until dried. The coated dishes are tested for antimicrobial activity against *E. coli*. Table 5 and FIG. 5B show the average bacterial removal rates of the two sets of petri dishes.

| Elapsing time | Average bacteria removal rate | | |
|---|---|---|---|
| | Spreading | Wiping to disperse | Wiping to dry |
| 1 min | 92.35% | 18.19% | −0.91% |
| 5 min | 100.00% | 44.02% | 12.87% |
| 10 min | 100.00% | 58.87% | 20.88% |
| 15 min | 100.00% | 65.05% | 22.18% |
| 30 min | 100.00% | 91.74% | 32.91% |
| 1 hr | 100.00% | 99.56% | 58.83% |
| 2 hrs | — | 100.00% | 80.22% |
| 3 hrs | — | 100.00% | 94.09% |

Table 5 shows the antimicrobial activity against *E. coli* of surfaces coated with the present coating composition after different application means Result shows that bacteria killing rate of coating by wiping method is lower than spreading. This is because certain amount of solution is removed by tissue during wiping. Moreover, over 99% of *E. coli* is killed at about 1 hour for sample with coating solution dispersed and air dried and about 94% of *E. coli* is killed in 3 hours for sample with coating solution wiping until dried. The present coating composition can be applied by wiping solution on surface or wiping until dried. The antibacterial efficacy is dependent on the amount of coating composition and method applied.

Example 5—Antimicrobial Efficiency—Other Microorganisms (1) *Staphylococcus aureus* is used as a representative of a gram-positive bacterium. Antimicrobial activity of the present coating composition against *Staphylococcus aureus* is investigated. *S. aureus* suspension at $5 \times 10^4$ cells/2 ml is spread onto a glass surface coated with 8.5 μl/cm² of the present coating composition, and an uncoated glass surface is tested together as control.

Samples are then incubated at room temperature for 1 hour. The bacteria removal rates at specified time points are determined.

| Elapsing time | Bacteria removal rate | | | |
|---|---|---|---|---|
| | Set 1 | Set 2 | Set 3 | Average |
| 1 min | 74.51% | 98.89% | 58.94% | 58.94% |
| 5 min | 100.00% | 100.00% | 100.00% | 100.00% |
| 10 min | 100.00% | 100.00% | 100.00% | 100.00% |
| 15 min | 100.00% | 100.00% | 100.00% | 100.00% |
| 30 min | 100.00% | 100.00% | 100.00% | 100.00% |
| 1 hour | 100.00% | 100.00% | 100.00% | 100.00% |

Figure 6:
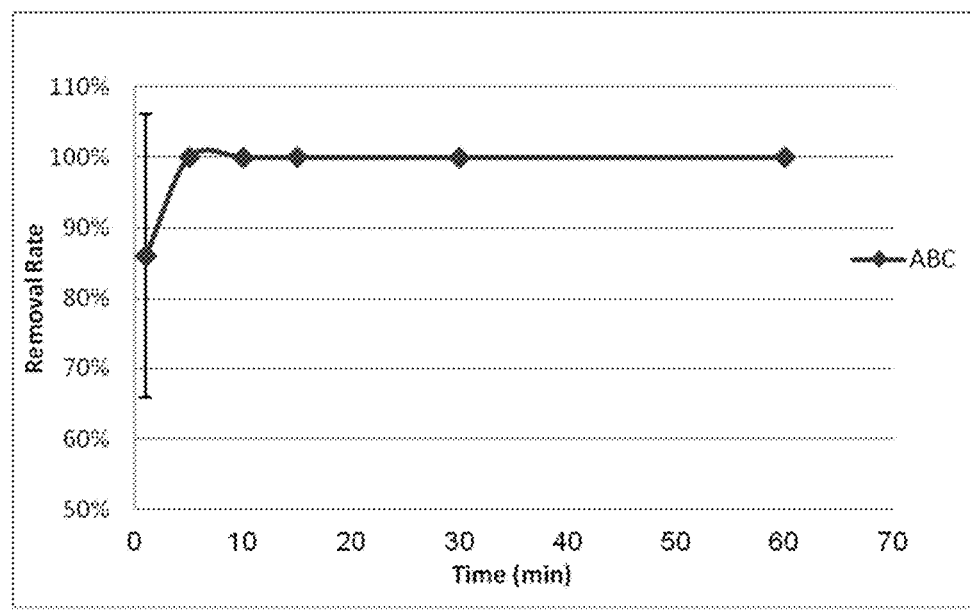
FIG. 6 is a graph showing the *S. aureus* removal rate of glass surface coated with a coating composition of the present invention.

Table 6 shows the antibacterial activity against *S. aureus* of surfaces coated with the present coating composition As seen in Table 6 and FIG. 6, surface coated with the present coating composition eliminates 100% *S. aureus* in 5 mins. It is shown that surfaces coated with the present coating composition eliminate at least 99.99% of gram-positive bacteria.

(2) Methicillin-resistant *Staphylococcus aureus* (MRSA) is the strain of *S. aureus* that has developed resistance to certain types of antibiotics. This kind of bacteria is difficult to treat.

Figure 7:
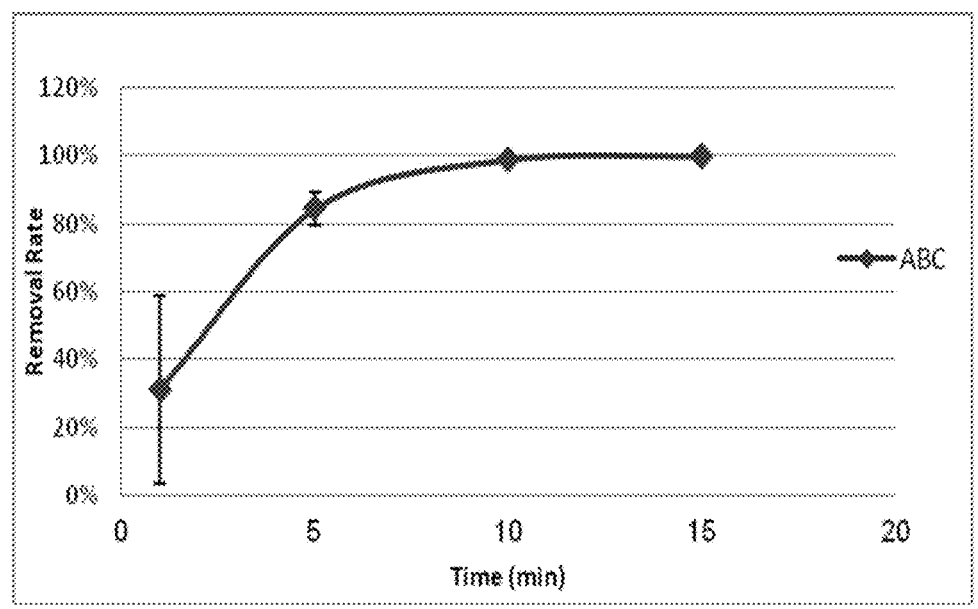
FIG. 7 is a graph showing the MRSA removal rate of glass surface coated with a coating composition of the present invention.

MRSA suspension is spread onto surface of petri dish coated with 8.5 μl/cm² of the present coating composition, and on an uncoated petri dish as a control. The coated and uncoated petri dishes are then incubated at room temperature for 15 minutes. The bacteria removal rates at specified time points are determined. Table 7 and FIG. 7 show that surfaces coated with the present coating composition can remove 100% MRSA in 15 mins. It is demonstrated that surface coated with the present coating composition is effective to remove 99.99% MRSA within 15 mins.

| Elapsing time | Bacteria removal rate | | | |
|---|---|---|---|---|
| | Set 1 | Set 2 | Set 3 | Average |
| 1 min | 52.17% | 41.86% | 0.00% | 31.34% |
| 5 min | 89.55% | 83.98% | 80.00% | 84.51% |
| 10 min | 98.48% | 100.00% | 98.20% | 98.89% |
| 15 min | 100.00% | 100.00% | 100.00% | 100.00% |

Table 7 shows the antibacterial activity against MRSA of surfaces coated with the present coating composition (3) *Klebsiella pneumoniae* has ability to produce extended spectrum beta-lactamases (ESBL) which are resistant to many classes of antibiotics. *K. pneumoniae* is tested as the representative for ESBL type microbes. ESBL suspension at $5 \times 10^4$ cells/2 ml is spread onto a glass surface coated with 8.5 μl/cm² of the present coating composition and on uncoated glass surface as control. The coated and uncoated glass surfaces are then incubated at room temperature for 30 minutes. The bacteria removal rates at specified time points are determined.

| Elapsing time | Bacteria removal rate | | | |
|---|---|---|---|---|
| | Set 1 | Set 2 | Set 3 | Average |
| 1 min | −1.74% | 10.95% | 6.38% | 5.20% |
| 5 min | 50.66% | 98.64% | 93.51% | 80.94% |
| 10 min | 100.00% | 100.00% | 100.00% | 100.00% |
| 15 min | 100.00% | 100.00% | 100.00% | 100.00% |
| 20 min | 100.00% | 100.00% | 100.00% | 100.00% |
| 30 min | 100.00% | 100.00% | 100.00% | 100.00% |

Figure 8:
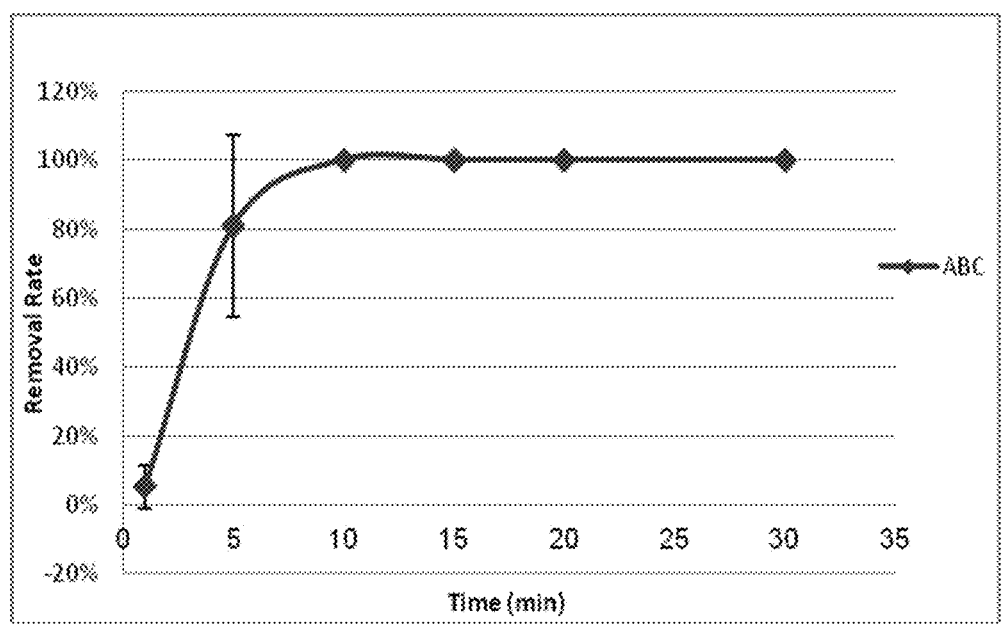
FIG. 8. is a graph showing the ESBL removal rate of glass surface coated with a coating composition of the present invention.
Figure 9:
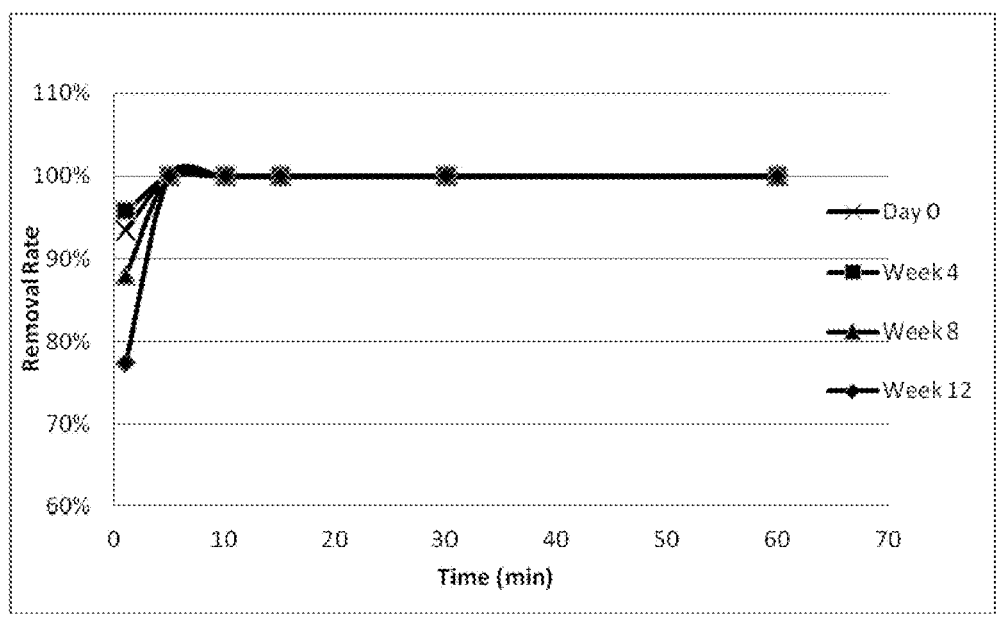
FIG. 9 is a graph showing bacterial removal rate of glass surface coated with a coating composition of the present invention having stored at room temperature for 0-12 weeks.

Table 8 shows the antimicrobial activity against ESBL of surfaces coated with the present coating composition As seen in Table 8 and FIG. 8, 100% of ESBL is eliminated by surface coated with the present coating composition in 10 mins. It is evident that the present coating composition eliminates at least 99.99% ESBL within 10 mins.

(4) The ability to kill endospore of the present coating composition is investigated. *Bacillus subtilis* (*B. subtilis*) has ability to form a tough and protective endospore, allowing the organism to tolerate extreme environmental conditions and thus the endospores are more difficult to be killed. The anti-endospore activity of surfaces coated with the present coating composition is tested in accordance with test standard, JIS Z 2801 "Antibacterial Products-Test for antibacterial activity and efficacy" at Castco Testing Centre Limited. Solution of *B. subtilis* endospore is dripped onto the surface coated with the present coating composition and on uncoated surface (control). The test coated and uncoated surfaces are incubated at room temperature for 1 hour. At specified time points, the bacterium solution are recovered and the bacterial endospore counts are determined (Table 9).

| | Initial bacterial count (CFU/piece) | Average bacterial count (CFU/piece) | | Bacterial Reduction (%) |
|---|---|---|---|---|
| Time Points | | Uncoated sample | Coated sample | |
| 30 min | $7.0 \times 10^5$ | $7.1 \times 10^5$ | $1.1 \times 10^3$ | 99.85% |
| 45 min | $7.0 \times 10^5$ | $7.2 \times 10^5$ | $8.0 \times 10^2$ | 99.89% |
| 60 min | $7.0 \times 10^5$ | $7.7 \times 10^5$ | $6.0 \times 10^2$ | 99.92% |

Table 9 shows the bacterial count and bacterial endospore reduction of *B. subtilis* on surfaces coated and uncoated with the present coating composition The results show that more than 99% of *B. subtilis* endospores are removed on surfaces coated with the present coating composition within 30 mins, and over 99.9% spores are removed within 60 mins. It is demonstrated that surface coated with the present coating composition is effective in killing bacterial spores.

(5) Anti-fungal activity of the present coating composition is assessed according to Standard BS3900-G6:1989 at Castco Testing Centre Limited. Table 10 is the list of fungi tested. Surfaces coated or uncoated with the present coating composition are tested with fungi for 6 weeks and the anti-fungal ability is measure on $1^{st}$, $2^{nd}$, $4^{th}$, and $6^{th}$ week.

| Species | Strain number |
|---|---|
| Aspergillus versicolor | IMI 45554 |
| Aureobasidium pullulans | IMI 45533 |
| Cladosporium cladosporioides | IMI 178517 |
| Penicillium purpurogenum | IMI 178519 |
| Phoma violacea | IMI 49948ii |
| Rhodotorula rubra | NCYC 1659 |
| Rhodotorula rubra | NCYC 1660 |
| Sporobolomyces roseus | NCYC 717 |
| Stachybotrys chartarum | IMI 82021 |
| Ulocladium atrum | IMI 79906 |

Table 10 shows fungal species that surfaces coated or uncoated with the present coating composition tested against.

The results show that no fungal growth is detected during the 6 weeks of incubation. It is evident that surface coated with the present coating composition can inhibit fungal growth for at least 6 weeks (Table 11).

| Time of incubation | Rating | Description |
|---|---|---|
| ABC coated sample | | |
| 1 week | 0 | No growth |
| 2 weeks | 0 | No growth |
| 4 weeks | 0 | No growth |
| 6 weeks | 0 | No growth |
| Uncoated sample | | |
| 2 weeks | 2 | More than 1%-10% |
| 4 weeks | 4 | More than 30%-70% |

Table 11 shows antifungal growth on surfaces coated or uncoated with the present coating composition for 6 weeks (6) Anti-virus activity of surfaces coated with the present coating composition is assessed by Standard test JIS Z 2801 at Kitasato Research Center for Environmental Science.

Influenza A virus (H1N1) is dripped onto coated surface, and uncoated surface. The test samples are then incubated at room temperature for 15 minutes, and viral solution is recovered and viral infectivity titers are measured at specific time points (Table 12). The results show that 99.9% virus is removed within 10 mins. It is evident that surface coated with the present coating composition is also anti-viral and kill more than 99.9% virus within 10 mins.

| | Reaction time | | | |
|---|---|---|---|---|
| Time points | 0 (initial) | 5 min | 10 min | 15 min |
| Uncoated sample | $1.2 \times 10^5$ | $7.0 \times 10^4$ | $8.5 \times 10^4$ | $9.5 \times 10^4$ |
| ABC coated | N.A. | $5.0 \times 10^2$ | $<1.0 \times 10^2$ | $<1.0 \times 10^2$ |
| Reduction ratio (%) | | 99.2 | >99.9 | >99.9 |

Table 12 shows the anti-influenza A virus efficacy of surfaces coated and uncoated with the present coating composition

Example 6—Stability of the Present Coating Composition and Surface Coated Therewith (1) Shelf life of the present coating composition is studied. The coating composition is stored at room temperature and anti-$E.$ $coli$ activity of the coating composition is tested after 4 weeks, 8 weeks and 12 weeks of storage. The coating composition is spread on glass surface to obtain at a concentration of 8.5 µl/cm². The test is performed in three replicates and the average bacterial removal rates are shown in Table 13 and FIG. 9. The results show surface coated with the coating composition after 4, 8 and 12 weeks of storage remove 100% of bacteria within 5 mins. It is evident that the present coating composition is stable for at least 12 weeks.

| | Average bacteria removal rate | | | |
|---|---|---|---|---|
| Elapsing time | Day 0 | Week 4 | Week 8 | Week 12 |
| 1 min | 93.37% ± 8% | 95.70% ± 2% | 88.05% ± 10% | 77.44% ± 4% |
| 5 min | 100.00% ± 0% | 100.00% ± 0% | 100.00% ± 0% | 100.00% ± 0% |
| 10 min | 100.00% ± 0% | 100.00% ± 0% | 100.00% ± 0% | 100.00% ± 0% |
| 15 min | 100.00% ± 0% | 100.00% ± 0% | 100.00% ± 0% | 100.00% ± 0% |
| 30 min | 100.00% ± 0% | 100.00% ± 0% | 100.00% ± 0% | 100.00% ± 0% |
| 1 hr | 100.00% ± 0% | 100.00% ± 0% | 100.00% ± 0% | 100.00% ± 0% |

Figure 10:
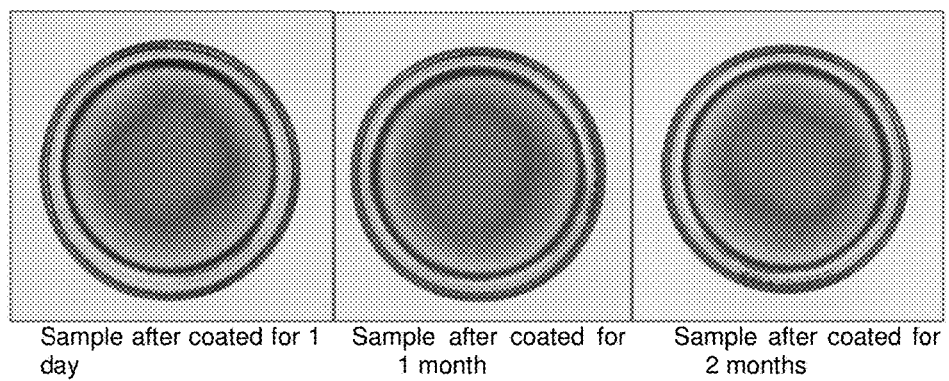
FIG. 10 is photographs showing glass surface coated with a coating composition of the present invention after coated for 1 day to 2 months.
Figure 11:
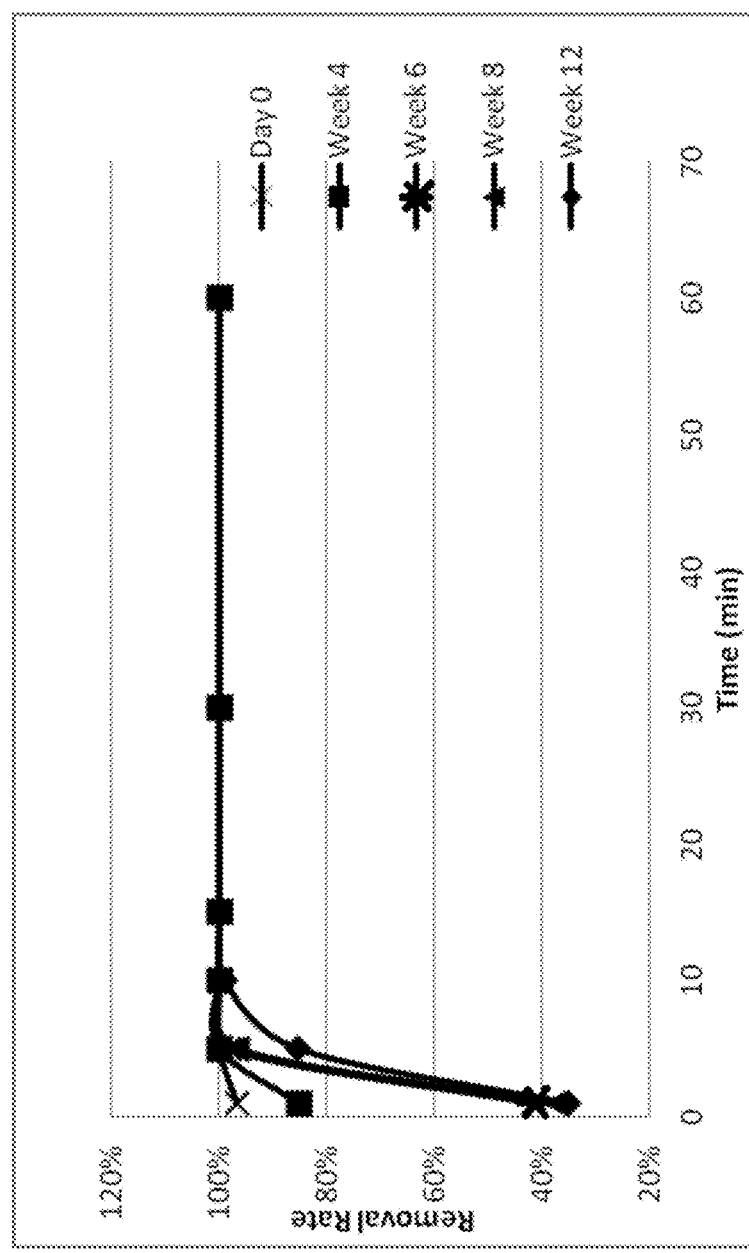
FIG. 11 is a graph showing the bacterial removal rate of glass surface coated with a coating composition of the present invention after coated for 0-12 weeks.

Table 13 shows antimicrobial activity of the present coating composition after storage (2) Stability of the coating formed from the present coating composition is investigated in terms of appearance and antibacterial activity. The present coating composition in blue dye is spread on glass petri dish at a concentration of 8.5 µl/cm². The coated petri dish is then stored at room temperature and ambient humidity without wiping for two months. As seen in FIG. 10, no change in the coated surface in appearance is observed after two months. It is demonstrated that surface coated with the present coating composition is stable in appearance for at least two months.

To study the stability of the antimicrobial activity of the coating formed from the present coating composition, the present coating composition is spread on glass petri dish at a concentration of 8.5 µl/cm². The coated petri dish is then stored at room temperature and ambient humidity without wiping for 4, 6, 8 and 12 weeks and then the coated petri dish obtained at each time point is tested for antimicrobial activity against $E.$ $coli$.

| Elapsing time | Bacteria removal rate | | | |
|---|---|---|---|---|
| | Week 4 | Week 6 | Week 8 | Week 12 |
| 1 min | 85.17% | 41.59% | 37.50% | 35.45% |
| 5 min | 100.00% | 98.26% | 96.67% | 85.49% |

-continued

| Elapsing time | Bacteria removal rate | | | |
|---|---|---|---|---|
| | Week 4 | Week 6 | Week 8 | Week 12 |
| 10 min | 100.00% | 100.00% | 100.00% | 99.08% |
| 15 min | 100.00% | 100.00% | 100.00% | 100.00% |
| 30 min | 100.00% | 100.00% | 100.00% | 100.00% |
| 1 hr | 100.00% | 100.00% | 100.00% | 100.00% |

Table 14 shows bacterial removal rate of surface coated with the present coating composition having stored for various time The results show that after 12 weeks of storage, the coating can remove 100% of the bacteria within 15 mins (Table 14). While it is seen that the antibacterial activity of the coated surface decreases as the storage time of the coating increases, exposing the coating in ambient environment has minimal effect in the antibacterial activity of the coating. The coated surface remains antimicrobial active after 12 weeks of storage.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

The invention claimed is:

1. A method of preparing a coating composition, comprising the steps of: providing a silver nanoparticle dispersion and chlorhexidine;

dissolving chitosan in an acidic organic solvent to form a chitosan solution; incubating a chitosan cross-linker with the chitosan solution to form a solution of cross-linked chitosan; and mixing the silver nanoparticle dispersion and chlorhexidine with the solution of crosslinked chitosan to form said coating composition, wherein the acidic organic solvent is acetic acid and the chitosan cross-linker is glutaraldehyde; and wherein said coating composition comprises 0.0002%-0.001% w/v of silver nanoparticles, 0.48%-1.9% w/v chitosan, 0.48-1.9% v/v acetic acid, 0.05%-0.2% v/v chlorhexidine and 0.06%-0.35% glutaraldehyde v/v.

2. A coating composition that forms a durable, stable and antimicrobial coating on a surface and air dries at room temperature without curing, wherein the coating composition is prepared by the method of claim 1.

3. The coating composition of claim 2, wherein the coating composition comprises 0.001% w/v of silver nanoparticles, 0.80% w/v chitosan, 0.80% v/v acetic acid, 020% v/v chlorhexidine, 0.24% v/v glutaraldehyde and 97.96% v/v water.

4. A method for depositing an antimicrobial coating onto at least a surface of an object comprising the steps of: providing an object, applying one or more layers of the coating composition prepared by the method of claim 1 onto said surface and, air drying the coating composition at room temperature without curing.

5. The method of claim 4, wherein said air drying the coating composition takes less than 60 mins.

6. The method of claim 4, wherein the antimicrobial coating has antimicrobial property comprising inhibiting growth of virus, fungi, gram-positive bacteria, gram-negative bacteria, MRSA and ESBL-type bacteria and endospore of bacteria.

7. The method of claim 4, wherein the surface comprises glass, wood, plastic, ceramic or metal.

8. The method of claim 4, wherein the applying comprises spraying or spreading.

9. A durable, stable and antimicrobial surface formed by the method of claim 4.

* * * * *